(12) United States Patent
Kalender et al.

(10) Patent No.: US 7,869,564 B2
(45) Date of Patent: Jan. 11, 2011

(54) X-RAY MACHINE FOR BREAST EXAMINATION HAVING A BEAM CONFIGURATION FOR HIGH RESOLUTION IMAGES

(75) Inventors: Willi Kalender, Moehrendorf (DE); Harry Schilling, Eichstaett (DE)

(73) Assignee: MIR Medical Imaging Research Holding GmbH, Moehrendorf (DE)

( * ) Notice: Subject to any disclaimer, the term of this patent is extended or adjusted under 35 U.S.C. 154(b) by 0 days.

(21) Appl. No.: 12/402,059

(22) Filed: Mar. 11, 2009

(65) Prior Publication Data

US 2010/0080348 A1 Apr. 1, 2010

(30) Foreign Application Priority Data

Sep. 29, 2008 (DE) .................. 10 2008 042 430

(51) Int. Cl.
*A61B 6/04* (2006.01)
(52) U.S. Cl. ........................................ 378/37; 378/98.8
(58) Field of Classification Search ............... 378/4–20, 378/37, 98.8
See application file for complete search history.

(56) References Cited

U.S. PATENT DOCUMENTS

| | | | |
|---|---|---|---|
| 3,673,394 A | 6/1972 | Hartmann |
| 4,015,836 A | 4/1977 | Redington et al. |
| 4,400,827 A | 8/1983 | Spears |
| 4,680,028 A | 7/1987 | Stuart |
| 4,709,382 A | 11/1987 | Sones |
| 5,273,435 A | 12/1993 | Jacobson |
| 5,308,321 A | 5/1994 | Castro |
| 5,386,447 A | 1/1995 | Siczek |
| 5,426,685 A | 6/1995 | Pellegrino et al. |
| 5,528,043 A | 6/1996 | Spivey et al. |

(Continued)

FOREIGN PATENT DOCUMENTS

DE 19639975 5/1998

(Continued)

OTHER PUBLICATIONS

Mun et al., "Active RFID System Augmented with 2D Barcode for Asset Management in a Hospital Setting," IEEE International Conference on RFID, Mar. 2007, pp. 205-211.

(Continued)

*Primary Examiner*—Courtney Thomas
(74) *Attorney, Agent, or Firm*—Kevin L. Daffer; Daffer McDaniel, LLP (57) ABSTRACT

An X-ray machine for imaging a breast of a female patient includes a patient table for accommodating the patient, an X-ray tube and an X-ray detector. In one embodiment, the X-ray machine may be designed as a spiral CT scanner having a rotatable gantry on which the X-ray tube and detector are mounted. The X-ray detector is inclined with respect to the X-ray tube, so that a central ray of a beam of rays emitted from the X-ray tube is perpendicularly incident on an active face of the detector. In one embodiment, the detector may be designed with a curvature, which reduces image artifacts by reducing path length differences between the central ray and the outer rays of the beam. This configuration provides particularly space saving X-ray machines, which at the same time, are of particularly high resolution.

13 Claims, 6 Drawing Sheets

U.S. PATENT DOCUMENTS

| | | | |
|---|---|---|---|
| 5,569,266 A | 10/1996 | Siczek | |
| 5,609,827 A | 3/1997 | Russell et al. | |
| 5,664,569 A | 9/1997 | Damadian et al. | |
| 5,757,878 A * | 5/1998 | Dobbs et al. | 378/19 |
| 5,803,912 A | 9/1998 | Siczek et al. | |
| 6,242,743 B1 | 6/2001 | DeVito et al. | |
| 6,254,614 B1 | 7/2001 | Jesseph | |
| 6,298,114 B1 | 10/2001 | Yoda | |
| 6,325,537 B1 | 12/2001 | Watanabe | |
| 6,358,246 B1 | 3/2002 | Behl et al. | |
| 6,415,012 B1 | 7/2002 | Taguchi et al. | |
| 6,418,188 B1 | 7/2002 | Broadnax | |
| 6,419,390 B1 | 7/2002 | Landis-Lowell | |
| 6,463,122 B1 | 10/2002 | Moore | |
| 6,480,565 B1 | 11/2002 | Ning | |
| 6,684,097 B1 | 1/2004 | Parel et al. | |
| 6,819,736 B1 | 11/2004 | Bruder et al. | |
| 6,837,772 B1 | 1/2005 | Luk | |
| 6,872,001 B1 | 3/2005 | Gilevich | |
| 7,005,988 B2 | 2/2006 | Mathewson, II et al. | |
| 7,065,393 B2 | 6/2006 | Sati et al. | |
| 7,304,578 B1 | 12/2007 | Sayers et al. | |
| 7,453,978 B1 | 11/2008 | DiBianca et al. | |
| 7,467,892 B2 | 12/2008 | Lang et al. | |
| 7,492,858 B2 | 2/2009 | Partain et al. | |
| 7,556,426 B2 | 7/2009 | Nakajo et al. | |
| 7,558,370 B2 | 7/2009 | Sommer, Jr. et al. | |
| 7,677,799 B2 | 3/2010 | Jensen et al. | |
| 7,697,660 B2 | 4/2010 | Ning | |
| 7,743,953 B2 | 6/2010 | Okazaki et al. | |
| 7,764,765 B2 | 7/2010 | Ohta et al. | |
| 2002/0181651 A1 | 12/2002 | Shepherd et al. | |
| 2003/0072409 A1 | 4/2003 | Kaufhold et al. | |
| 2003/0204965 A1 | 11/2003 | Hennessey | |
| 2004/0066880 A1 | 4/2004 | Oikawa | |
| 2004/0082856 A1 | 4/2004 | Marmarelis | |
| 2004/0092826 A1 | 5/2004 | Corbeil et al. | |
| 2004/0238750 A1* | 12/2004 | Vafi et al. | 250/370.11 |
| 2004/0251419 A1 | 12/2004 | Nelson et al. | |
| 2004/0254461 A1 | 12/2004 | Ackerman, III | |
| 2005/0070817 A1 | 3/2005 | Mueller, Jr. | |
| 2006/0094950 A1 | 5/2006 | Ning | |
| 2006/0145871 A1 | 7/2006 | Donati et al. | |
| 2006/0262898 A1 | 11/2006 | Partain et al. | |
| 2007/0009080 A1 | 1/2007 | Mistretta | |
| 2007/0064867 A1 | 3/2007 | Hansen et al. | |
| 2007/0092059 A1 | 4/2007 | Wayne Eberhard et al. | |
| 2007/0237306 A1 | 10/2007 | Jones et al. | |
| 2007/0238957 A1 | 10/2007 | Yared | |
| 2008/0033420 A1 | 2/2008 | Nields et al. | |
| 2008/0037703 A1 | 2/2008 | Ting | |
| 2008/0081984 A1 | 4/2008 | Lafferty | |
| 2008/0084961 A1 | 4/2008 | Keppel et al. | |
| 2008/0089471 A1 | 4/2008 | Kobayashi | |
| 2008/0101538 A1 | 5/2008 | Schliermann | |
| 2008/0187095 A1 | 8/2008 | Boone et al. | |
| 2008/0205588 A1* | 8/2008 | Kim | 378/20 |
| 2008/0221443 A1 | 9/2008 | Ritchie et al. | |
| 2008/0221478 A1 | 9/2008 | Ritchie et al. | |
| 2008/0230074 A1 | 9/2008 | Zheng et al. | |
| 2009/0080604 A1 | 3/2009 | Shores et al. | |
| 2009/0196393 A1 | 8/2009 | Wang et al. | |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Nishide et al., "Micro-focus x-ray CT imaging of breast specimens with microcalcifications," 89th Scientific Assembly and Annual Meeting of the Radiological Society of North America, Dec. 2003, pp. 1662-1663.

Tornai et al., "Design and Development of a Fully-3D Dedicated X-ray Computed Mammotomography System," Proceedings of SPIE, vol. 5745, 2005, pp. 189-197.

Bentzen et al., "Isothem mapping in hyperthermia using subtraction X-ray computed tomography," Radiotherapy and Oncology, vol. 2, 1984, 255-260.

Griffiths et al., "Applied potential tomography for non-invasive temperature mapping in hyperthermia," Clin. Phys. Physiol. Meas., vol. 8, Suppl. A, 1987, pp. 147-153.

Jenne et al, "CT On-Line Monitoring of HIFU Therapy," IEEE Ultrasonics Symposium, 1997, pp. 1377-1380.

Fallone et al., "Noninvasive thermometry with a clinical x-ray CT scanner," Med. Phys., vol. 9, No. 5, 1982, pp. 715-721.

Office Action mailed Nov. 3, 2009 for U.S. Appl. No. 12/401,765.

Notice of Allowance mailed Apr. 15, 2010 for U.S. Appl. No. 12/401,765.

Office Action mailed Apr. 1, 2010 for U.S. Appl. No. 12/402,141.

Office Action mailed Jun. 16, 2010, for U.S. Appl. No. 12/401,906.

Office Action mailed Jun. 10, 2010, for U.S. Appl. No. 12/401,735.

Offie Action mailed Jul. 13, 2010, for U.S. Appl. No. 12/402,225.

Office Action mailed May 11, 2010, for U.S. Appl. No. 12/401,814.

Office Action mailed Sep. 23, 2010 for U.S. Appl. No. 12/401,792.

Notice of Allowance mailed Aug. 23, 2010 for U.S. Appl. No. 12/401,765.

* cited by examiner

X-RAY MACHINE FOR BREAST EXAMINATION HAVING A BEAM CONFIGURATION FOR HIGH RESOLUTION IMAGES

PRIORITY CLAIM

This application claims priority to pending German Application No. DE102008042430.7 filed on Sep. 29, 2008.

BACKGROUND OF THE INVENTION

1. Field of the Invention

The invention relates to an X-ray machine for imaging a female breast (mammography). In particular, the invention relates to a machine with which high-resolution X-ray exposures may be produced.

2. Description of Related Art

X-ray machines with an X-ray tube and a detector of large surface are known from prior art. For example, an X-ray machine is disclosed in U.S. Pat. No. 6,480,565, in which the size of the detector is dimensioned so that an entire breast can be imaged. In order to produce three-dimensional images, the X-ray tube and the detector are located on a rotatable gantry, which permits exposures to be made from different angular positions. Another X-ray machine, which is based on a spiral computer tomography (CT) scanner, is disclosed in U.S. Publication No. 2007/0064867. In this X-ray machine, exposures are made continuously during rotation of a gantry comprising an X-ray tube and a detector. However, a relatively large region of a wall of a breast cannot be imaged with the X-ray machine disclosed in the US publication.

BRIEF SUMMARY OF THE INVENTION

The following description of the objective of the disclosure provided herein and the description of an embodiment of an X-ray machine for imaging a breast is not to be construed in any way as limiting the subject matter of the appended claims.

An objective of the disclosure provided herein is to design an X-ray machine, which images a female breast in a diagnostically correct manner, rapidly, at favorable cost, and with high resolution. Another object of the disclosure is to design an X-ray detector for an X-ray machine of this kind.

An embodiment of an X-ray machine for imaging a breast of a female patient includes a support surface for the patient, an X-ray tube for emitting a beam of rays at an angle $2\alpha$, and an X-ray detector for detecting radiation, which is emitted by the X-ray tube and passed through the breast of the female patient. The X-ray detector is inclined at an angle $\alpha$ with respect to an axis, which is perpendicular to the support surface, so that a central ray of the beam of rays is incident on a middle of the X-ray detector at a 90° angle.

In one embodiment, the X-ray machine comprises a gantry, which is coupled to the support surface and rotatable about a rotational axis extending perpendicular to the support surface. In such an embodiment, the X-ray detector is inclined at an angle $\alpha$ with respect to the rotational axis of the gantry, so that a central ray of the beam of rays is incident on the middle of the X-ray detector at a 90° angle.

An embodiment of an X-ray detector for an X-ray machine for imaging a breast of a female patient includes an arcuate tiled detector, which comprises an arcuate detector support on which detector tiles are mounted by means of detector holders. The detector holders enable the detector tiles to be individually positioned on the arcuate detector support, and thus, individually aligned with respect to the beam of rays. It is generally desired that the detector tiles be positioned so that they partially overlap.

In one embodiment, each detector holder includes a clamping plate coupled to the arcuate detector support, a plurality of retaining plates coupled to a back surface of a detector tile, an elastic ring positioned between the back surface of the detector tile and the clamping plate, and a plurality of bolts, each threaded through one of the retaining plates and the clamping plate to fasten the detector tile to the clamping plate with the elastic ring positioned there between. In this embodiment, each of the plurality of bolts is independently adjustable for adjusting an orientation of the detector tile.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Figure 1:
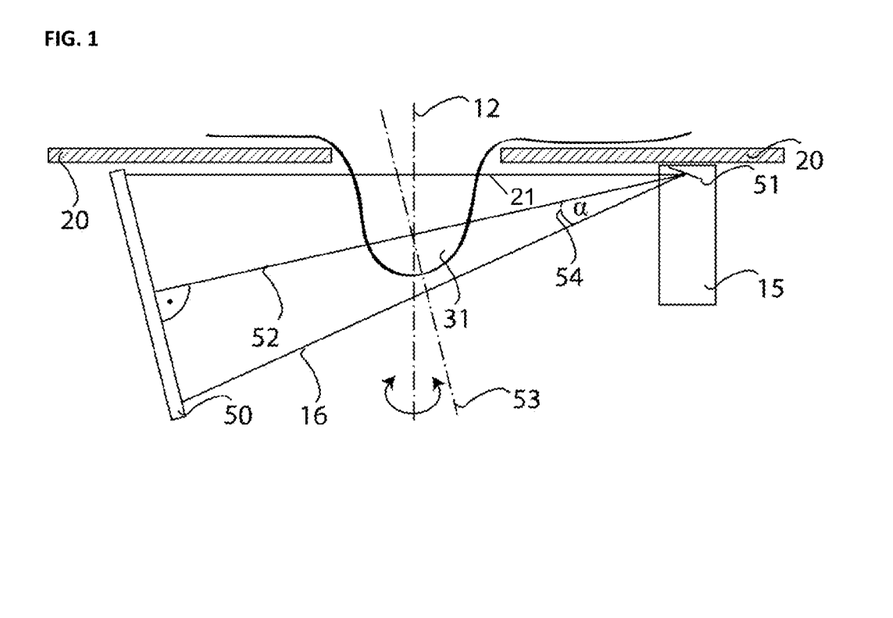
FIG. 1 shows a partial cross-sectional view of a gantry of an X-ray machine having a flat panel detector, which is tilted relative to the rotational axis of the gantry.

FIG. 1 illustrates an embodiment of an X-ray machine having a flat panel detector 50. A patient's breast 31 to be examined is suspended through an opening 21 in a support surface, which in this embodiment is a patient table 20. Of course, this arrangement may also be rotated through a range of desired angles, resulting in an alternative arrangement in which the patient table 20 is inclined or stood up on end. In such an arrangement, the inclined or stood up patient table may only be an abutting surface through which a breast is inserted. In either embodiment, it is desired that chest wall of the patient rest as close as possible to the patient table 20, so that the breast can be imaged as completely as possible.

The X-ray machine shown in FIG. 1 includes a gantry (not shown in FIG. 1) rotating about a rotational axis 12. Among other components, the rotating gantry includes an X-ray tube 15 and a flat panel detector 50. The anode 51 within the X-ray tube 15 generates a beam of rays 16, which penetrates the breast 31 and is received by the flat panel detector 50. The beam of rays 16 is restricted to the active face of the detector 50. It is generally not desired that the beam penetrate the patient table 20.

As shown in FIG. 1, the entire beam of rays 16 has an angle $2\alpha$ and a one-half beam angle $\alpha$ 54. In addition, the flat panel detector 50 is tilted relative to the rotational axis 12 of the gantry. In particular, the flat panel detector 50 is tilted at the angle $\alpha$ in a direction towards the X-ray tube. Tilting the detector by the half angle $\alpha$ causes the central ray 52 in the middle of the beam of rays 16 to be perpendicularly incident on the surface of the flat panel detector 50 in the middle of the flat panel detector 50. Tilting the detector by the half angle $\alpha$ also causes the central axis 53 of the beam of rays 16, which is defined as the axis perpendicular to the central ray 52, to be at an angle $\alpha$ to the rotational axis 12.

Of course, the flat panel detector shown in FIG. 1 is a plane drawing of a three-dimensional structure, which also has an extension perpendicular to the plane of the drawing. The characterization of the middle of the flat panel detector 50 relates in this drawing to the middle of its dimension parallel to the plane of the drawing. By tilting the detector as shown in FIG. 1, the path length differences between the central ray 52 and the outer rays of the beam 16 are smaller than the path length differences produced by an X-ray machine comprising a non-tilted detector.

Figure 2:
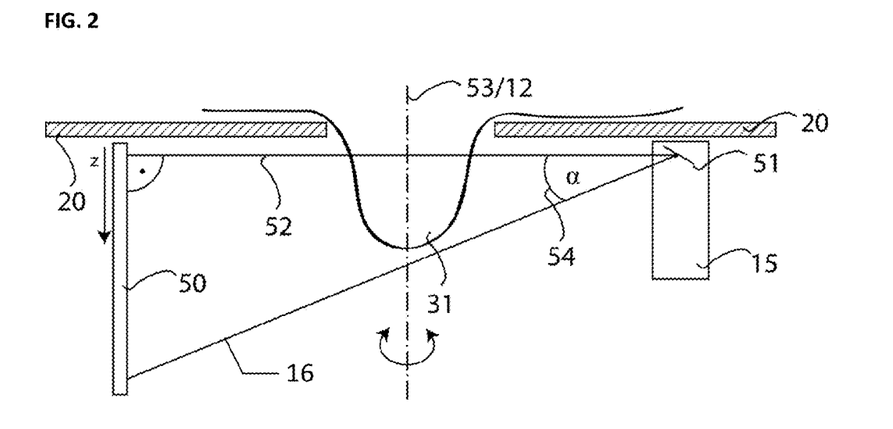
FIG. 2 shows a partial cross-sectional view of a gantry of an X-ray machine having a flat panel detector, which is not tilted.

FIG. 2 illustrates an embodiment of an X-ray machine having a non-tilted detector. The embodiment shown in FIG. 2 includes many of the components shown in FIG. 1 and described above. Components with like numerals will not be described herein for the sake of brevity.

The embodiment shown in FIG. 2 generally differs from the embodiment of FIG. 1 in that the flat panel detector is not tilted relative to the rotational axis 12 of the gantry. Instead, the flat panel detector 50 is disposed parallel to the rotational axis 12 and perpendicular to the patient table 20. In a non-tilted arrangement, the central axis 53 extends parallel to the rotation axis 12, resulting in a rather simple evaluation of the image generated by the X-ray machine of FIG. 2. However, artifacts arise in the image due to the difference of path lengths between that of the shortest ray (which in this case is the central ray 52 perpendicularly incident on the flat panel detector 50 at the upper end thereof) and that of the longest ray at the lower end of the detector 50.

Figure 3:
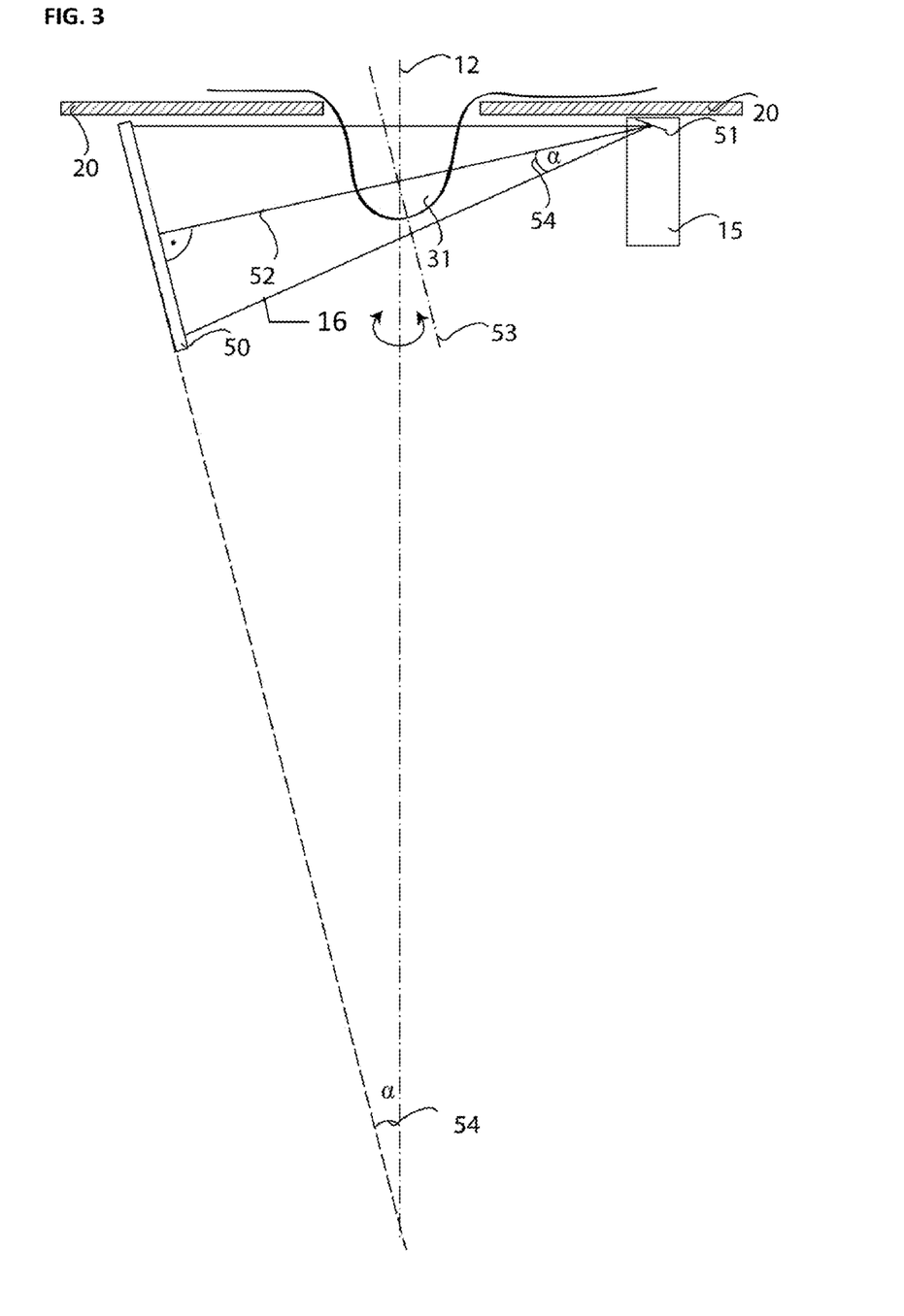
FIG. 3 illustrates the angular relationships of the X-ray machine shown in FIG. 1 in more detail.

FIG. 3 illustrates in more detail the angular relationships exhibited by the X-ray machine shown in FIG. 1. FIG. 3 shows that if an imaginary extension of the surface of the flat panel detector 50 were drawn, the imaginary line would intercept the rotational axis 12 of the gantry at the half angle $\alpha$ 54.

Figure 4:
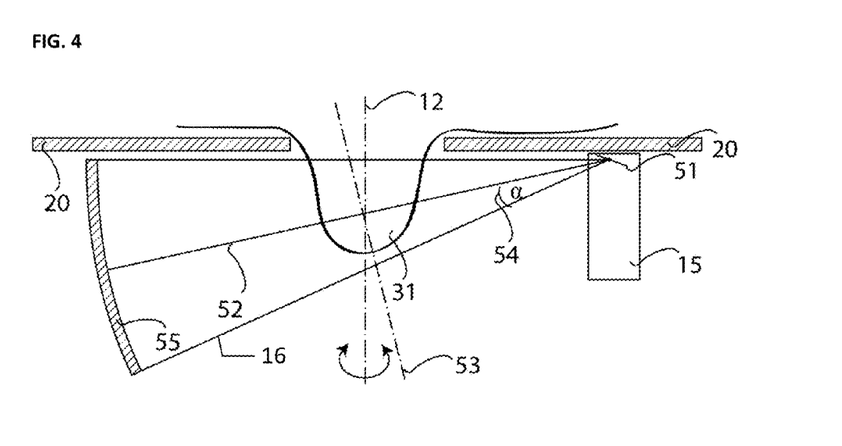
FIG. 4 shows a partial cross-sectional view of an X-ray machine having an arcuate detector.

FIG. 4 illustrates an alternative embodiment of an X-ray machine having an arcuate detector 55. The difference in path lengths between the shortest ray (central ray 52) and the longest ray (at the upper and lower end of the beam 16) is further reduced due to the curvature of the detector. In one embodiment, the curvature is designed so that all rays (not just the central ray 52) will be incident on the detector at right angles. Such an arrangement minimizes artifacts in the image generated by the X-ray machine of FIG. 4 by minimizing path length differences.

Figure 5:
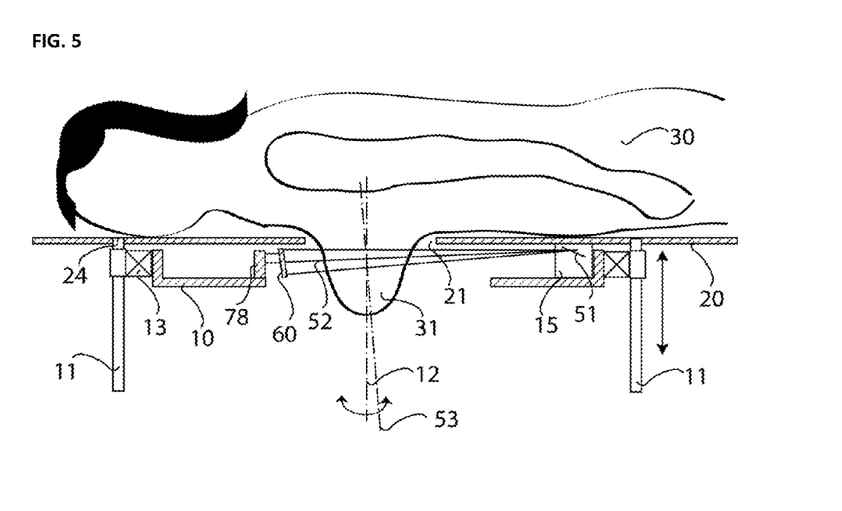
FIG. 5 shows a partial cross-sectional view of an X-ray machine designed as a spiral computer tomography (CT) scanner.

FIG. 5 illustrates an embodiment of an X-ray machine designed to be a spiral computer tomography (CT) scanner. As shown in FIG. 5, the spiral CT scanner comprises a gantry 10, which accommodates an X-ray tube 15 and a tilted arcuate detector 60 on a detector support 78. For imaging a breast 31, the gantry 10 can be set into continuous rotational motion. Furthermore, it can be linearly displaced perpendicularly to the rotational axis 12, whilst being synchronized with the rotation. A substantially compact detector 60 can be used, since the breast 31 is scanned along individual spiraling tracks. The use of a compact detector enables the detector to be positioned substantially closer to the patient table 20, thus, enabling a larger region of the breast 31 to be imaged close to the breast wall.

Figure 6:
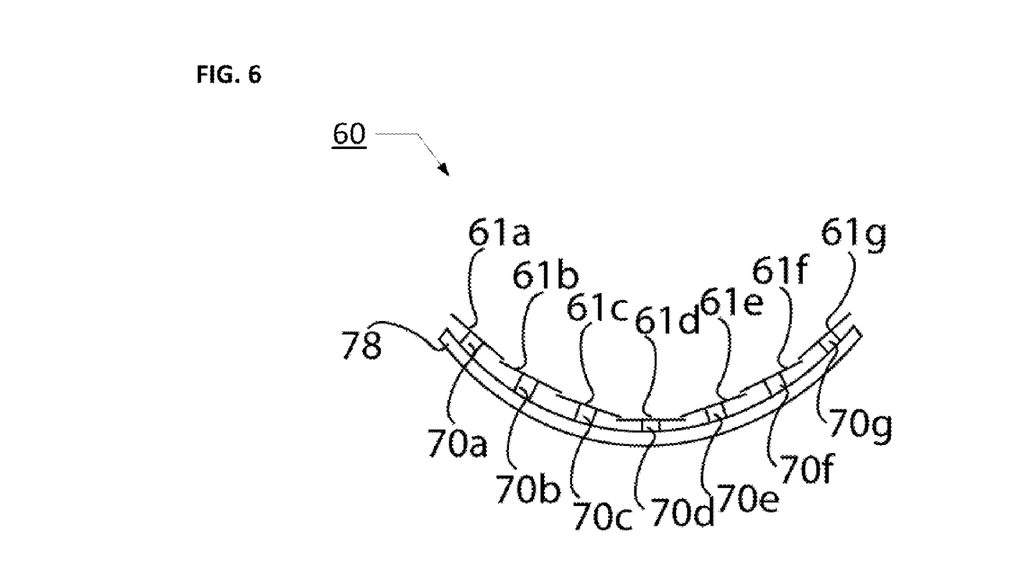
FIG. 6 shows a plan view of a tiled arcuate detector.

FIG. 6 illustrates a magnified plan view of a tilted arcuate detector 60. As noted above and shown in FIG. 5, the tilted detector comprises a detector support 78 on which a number of plane detector tiles 61a-61g are mounted. Each of the detector tiles comprise at least one highly resolving semiconductor X-ray detector. The detector support 78 determines the basic shape of the arcuate detector. Preferably, the detector tiles overlap slightly so that connecting regions at the edge of each tile will lie underneath an adjacent tile. This permits imaging without gaps. In one embodiment, the individual detector tiles 61a-61g are attached to the detector support 78 by means of detector holders 70a-70g. The detector holders are preferably designed to be adjustable. This enables an orientation of the detector tiles to be adjusted with the detector holders.

Figure 7:
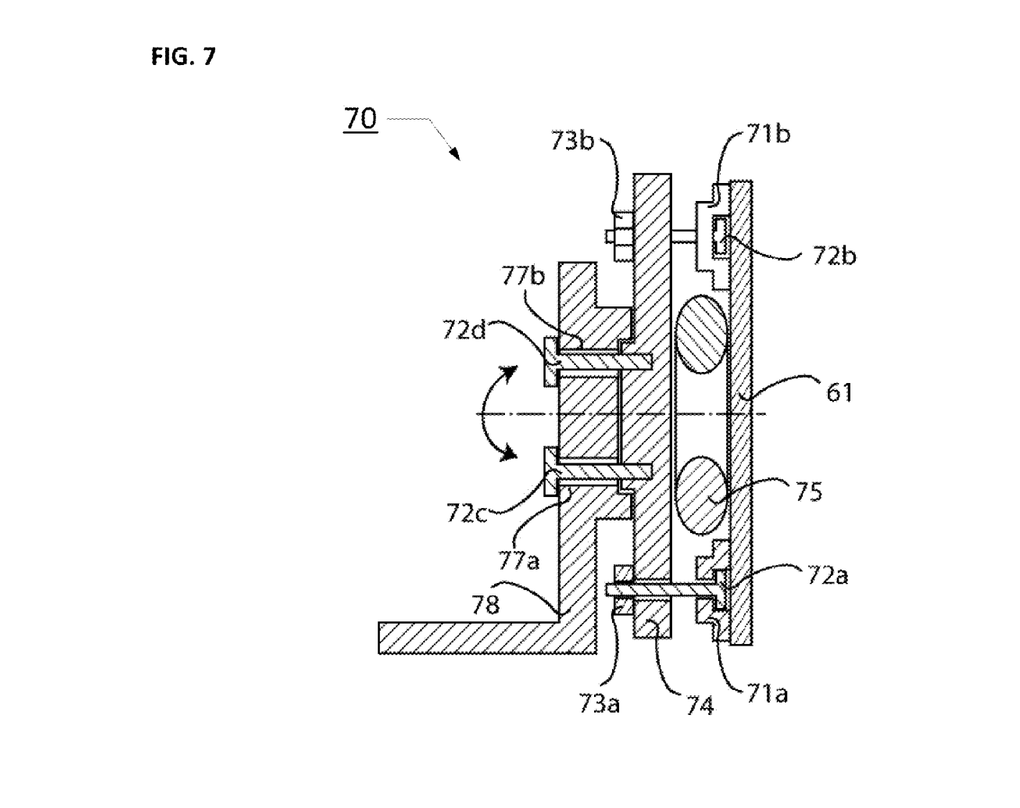
FIG. 7 shows a cross-sectional view through a detector holder.

FIG. 7 illustrates a cross-sectional view through an embodiment of detector holder 70. As shown in FIG. 7, the detector holder connects a detector tile 61 to the detector support 78 by fastening a clamping plate 74 to the detector support 78 by means of screws 72d, 72c. Screw holes 77a, 77b permit the clamping plate to be slightly rotated relative to the detector support. A rubber ring 75, which in one embodiment may be an O-ring, is inserted between the detector tile 61 and the clamping plate 74. The detector tile 61 is clamped against the elastic rubber ring by means of bolts 72a, 72b, which are fastened to the detector tile 61 via retaining plates 71a, 71b and nuts 73a, 73b. Although not shown in FIG. 7, three bolts 72 are preferably used to fasten the detector tile 61 to the retaining plate, so that the detector tile 61 can be oriented in all three directions. Two bolts 72a, 72b are shown in the Figure with bolt 72b lying in a plane behind the cross-section illustrated in the Figure. The third bolt is not shown for purposes of drawing clarity. Following its assembly, the detector holder 70 may be fixed, for example, by means of an adhesive. In one embodiment, a two-component mixed adhesive may be used on the detector holder.

Figure 8:
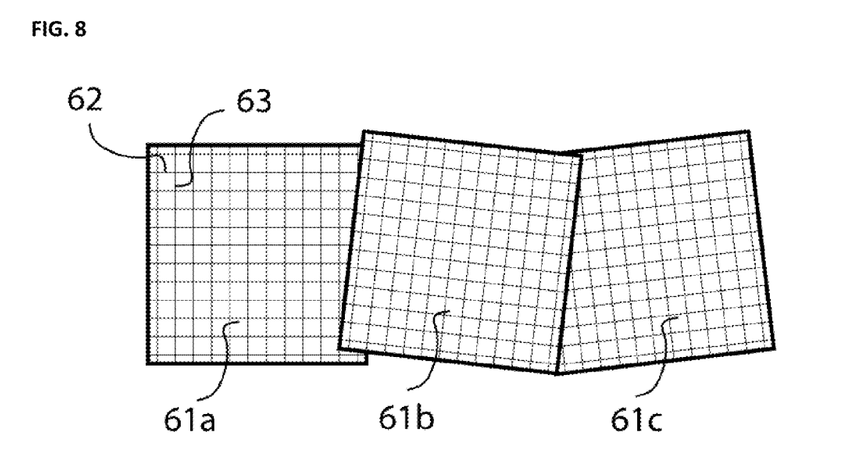
FIG. 8 shows a plan view of a plurality of individually adjustable detector tiles.

FIG. 8 illustrates a magnified plan view of a portion of the detector tiles 61 of the tiled arcuate detector 60. In this illustration, each one of the tiles has horizontally extending detector rows 62 and vertically extending detector columns 63 of individual detector elements. The size of a detector element of this kind is typically in a range of about 10 micrometers to about 500 micrometers, and in one embodiment, may be about 100 micrometers. As the individual detector tiles 61a, 61b, 61c have fabrication tolerances, they must be individually aligned or positioned with respect to the beam of rays 16. Furthermore, it is desirable that the detector tiles 61a, 61b, 61c overlap slightly, because non-imaging connecting elements (not illustrated here) are present at the edges of the individual detector tiles.

Figure 9:
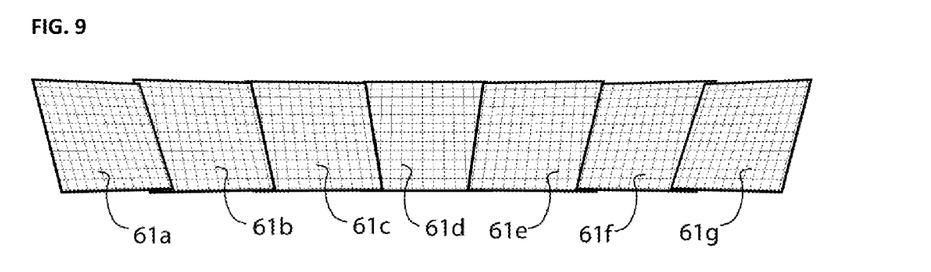
FIG. 9 shows a perspective view of a tiled arcuate detector as seen from an X-ray tube.

FIG. 9 illustrates an embodiment of a portion of a tiled arcuate detector 60 as viewed from the X-ray tube 15. The perspective view provided in FIG. 9 illustrates the individually positioned detector tiles 61a-g and the overlapping provided there between.

Figure 10:
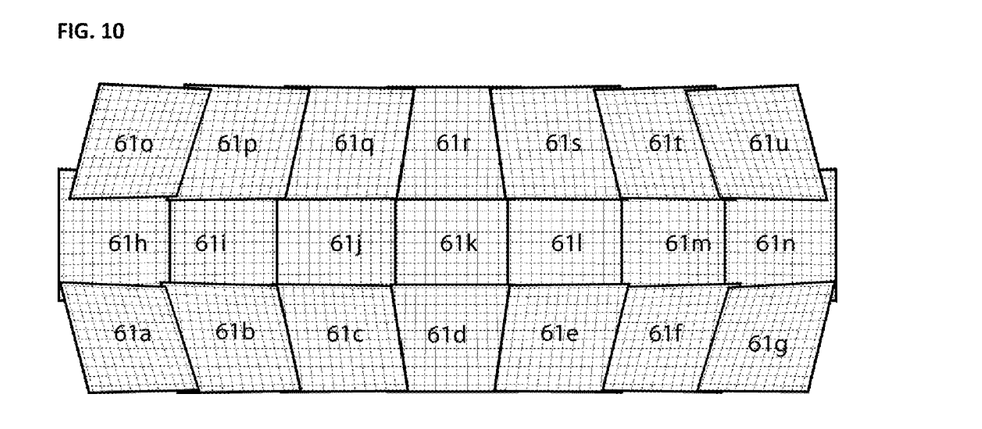
FIG. 10 shows a perspective view of another tiled arcuate detector having a plurality of detector elements arranged in three rows.

FIG. 10 is a perspective view of another tiled arcuate detector 60 as viewed from the X-ray tube 15. Three overlapping rows of detector tiles 61 are provided in the embodiment of FIG. 10. The upper row of detector tiles 61o-61u is tilted with respect to the middle row of detector tiles 61h-61n. The lower row detector tiles 61a-61g is also tilted with respect to the middle row of detector tiles 61h-61n, albeit in a different direction than the tilt direction of the upper row. The tilted upper and lower rows result in an approximation to an arcuate or arched detector structure.

Figure 11:
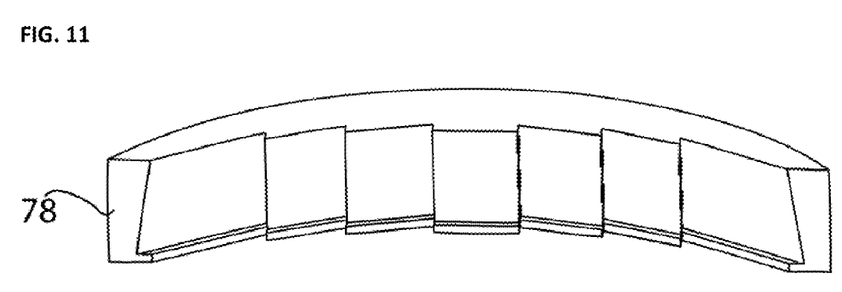
FIG. 11 shows an embodiment of a one-piece detector support.

FIG. 11 illustrates an embodiment of a detector support, which has been made of aluminum. The support shown in FIG. 11 has accommodating faces for fastening individual detector tiles.

As set forth above, an X-ray machine for imaging a female breast 31 comprises an X-ray tube 15 and an X-ray detector (e.g., detector 50, FIGS. 1 and 3, detector 55, FIG. 4, and detector 60, FIGS. 5-10). The X-ray tube 15 emits a beam of rays 16, which passes through the breast 31 onto the X-ray detector. The beam of rays 16 is ideally dimensioned so that it just covers the entire active face of the X-ray detector. In the following, reference is made only to a beam of rays of this kind. If the beam of rays were larger, then only that part of the beam of rays which covers the active detector face is relevant to the disclosure provided herein. In order for exposures to be made as closely as possible to the wall of the breast, an outer ray of the beam is arranged as close as possible to the breast wall. Because the breast wall rests upon a support surface such as, for example, a patient table, the outer ray of the beam lies approximately parallel to the support surface 20. Accordingly, the outer ray of the beam is preferably arranged parallel to the support surface 20 and/or geometrically bounded by a surface parallel to this support surface 20.

In one embodiment, the X-ray tube and X-ray detector of an X-ray machine may be in fixed positions during an exposure. In such an embodiment, the beam of rays 16 is emitted by the X-ray tube 15 at an angle of $2\alpha$ in a direction perpendicular to the support surface 20. To avoid artifacts in the image (e.g., cone beam artifacts), which are caused by different path lengths of radiation from the X-ray tube to the detector, the X-ray detector is inclined or tilted at the half angle $\alpha$ with respect to an axis that is perpendicular to the support surface 20 and approximately parallel to the breast wall.

In another embodiment, the X-ray tube and X-ray detector of an X-ray machine are disposed on a gantry 10 which rotates about a rotational axis 12. In such an embodiment, the X-ray detector is inclined at an angle $\alpha$ with respect to the rotational axis 12 of the gantry. As in the previous embodiment, the angle $\alpha$ is one half of the beam angle ($2\alpha$) emitted by the X-ray tube 15. If an imaginary extension of the face of the X-ray detector were drawn, the imaginary line would intersect the rotational axis 12 below the support surface 20 at an angle $\alpha$.

In either embodiment of the X-ray machine mentioned above (i.e., machines comprising fixed or rotating gantries), an arrangement results in which the central ray 52 of the beam 16 is perpendicularly incident on the center of the X-ray detector. This arrangement reduces the path length differences between the central ray and the outer rays at the edge of the detector.

In one embodiment, the X-ray tube and the X-ray detector are disposed on a rotatable gantry 10, which can be set into continuous rotational movement. The gantry can also be moved in a linear direction (i.e., parallel to the rotational axis 12) in synchronization with the rotational movement. Such a gantry typically corresponds to the gantry of a spiral computer tomograph.

In one embodiment, the beam of rays 16 is disposed parallel to the support surface 20, and/or geometrically bounded by a surface parallel to the support surface 20.

In one embodiment, the X-ray detector is designed to be arcuate, so that all rays—including the central ray 52 of the beam of rays 16 and other rays traveling laterally above and below the central ray—are perpendicularly incident on the active face of the detector.

In one embodiment, the X-ray detector is a tiled arcuate detector. A detector of this kind comprises an arcuate detector support 78. Detector tiles 61 are attached to the detector support 78 by means of detector holders 70. It is generally desired that adjacent detector tiles overlap to ensure imaging without gaps. It is of particular advantage when single detector tiles overlap each other like roof-tiles. The curvature of the arcuate detector support 78 is preferably configured so that the detector tiles attached thereto form an arc having a radius corresponding to the distance of the detector from the X-ray tube 15.

It will be appreciated to those skilled in the art having the benefit of this disclosure that this disclosure is believed to provide X-ray machines for imaging a breast. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An X-ray machine for imaging a breast of a female patient, comprising:

a support surface for the female patient;

a gantry rotatable about a rotational axis;

an X-ray tube attached to the gantry for emitting a beam of rays from an anode at an angle $2\alpha$, wherein the beam of rays is bounded by a plane parallel to the support surface; and an X-ray detector attached to the gantry for detecting radiation emitted by the X-ray tube and passed through the breast of the female patient, wherein the X-ray detector is inclined at an angle $\alpha$ with respect to the rotational axis so that a central ray of the beam of rays is incident on a middle of the X-ray detector at an approximately 90° angle.

2. The X-ray machine according to claim 1, wherein the gantry is adapted to be set into continuously rotational movement for imaging the breast, and wherein the gantry is moveable in a linear direction parallel to the rotational axis, wherein said movement in the linear direction is performed in synchronization with the rotational movement.

3. The X-ray machine according to claim 1, wherein the X-ray detector comprises an arcuate shape.

4. The X-ray machine according to claim 1, wherein the X-ray detector is a tiled arcuate detector comprising an arcuate detector support on which detector tiles are mounted by means of detector holders.

5. The X-ray machine according to claim 3, wherein the detector tiles partially overlap.

6. An X-ray machine for imaging a breast of a female patient, comprising:
   a support surface for the patient;
   an X-ray tube for emitting a beam of rays from an anode which has an angle $2\alpha$, wherein the beam of rays is bounded by a face parallel to the support surface; and
   an X-ray detector for detecting radiation emitted by the X-ray tube and passed through the breast of the female patient, wherein the X-ray detector is inclined at an angle $\alpha$ to the perpendicular to the support surface so that a central ray of the beam of rays is incident at an approximate right angle on a middle of the X-ray detector.

7. The X-ray machine according to claim 6, wherein the X-ray detector is of an arcuate shape.

8. The X-ray machine according to claim 6, wherein the X-ray detector is a tiled arcuate detector comprising an arcuate detector support on which detector tiles are mounted by means of detector holders.

9. The X-ray machine according to claim 8, wherein the detector tiles partially overlap.

10. An X-ray detector for an X-ray machine for imaging a breast of a female patient, wherein the X-ray detector is a tiled arcuate detector which comprises an arcuate detector support on which a plurality of detector tiles are mounted by means of a plurality of detector holders, wherein each detector holder comprises:
    a clamping plate coupled to the arcuate detector support;
    a plurality of retaining plates coupled to a back surface of a detector tile;
    an elastic ring positioned between the back surface of the detector tile and the clamping plate; and
    a plurality of bolts, each threaded through one of the retaining plates and the clamping plate to fasten the detector tile to the clamping plate with the elastic ring positioned there between.

11. The X-ray detector according to claim 10, wherein the detector tiles partially overlap.

12. The X-ray detector according to claim 10, wherein the detector holders enable the detector tiles to be individually positioned on the arcuate detector support, and thus, individually aligned with respect to the beam of rays.

13. The X-ray detector according to claim 10, wherein each of the plurality of bolts is independently adjustable for adjusting an orientation of the detector tile.

* * * * *

UNITED STATES PATENT AND TRADEMARK OFFICE
CERTIFICATE OF CORRECTION

| | | |
|---|---|---|
| PATENT NO. | : 7,869,564 B2 | |
| APPLICATION NO. | : 12/402059 | |
| DATED | : January 11, 2011 | |
| INVENTOR(S) | : Kalender et al. | |

It is certified that error appears in the above-identified patent and that said Letters Patent is hereby corrected as shown below:

Claim 5 at col. 7, line 5: After "according to" delete "claim 3" and substitute --claim 4--.

Signed and Sealed this
Fourteenth Day of June, 2011

David J. Kappos
*Director of the United States Patent and Trademark Office*